(12) United States Patent
Okuno et al.

(10) Patent No.: US 10,004,519 B2
(45) Date of Patent: Jun. 26, 2018

(54) JIG FOR GUIDE PIN PIERCING

(71) Applicants: TEIJIN MEDICAL TECHNOLOGIES CO., LTD, Osaka (JP); NATIONAL UNIVERSITY CORPORATION KOBE UNIVERSITY, Hyogo (JP)

(72) Inventors: Masaki Okuno, Osaka (JP); Hiroshi Morii, Osaka (JP); Katsuya Nada, Osaka (JP); Ryosuke Kuroda, Hyogo (JP)

(73) Assignees: TEIJIN MEDICAL TECHNOLOGIES CO., LTD, Osaka (JP); NATIONAL UNIVERSITY CORPORATION KOBE UNIVERSITY, Hyogo (JP)

( * ) Notice: Subject to any disclaimer, the term of this patent is extended or adjusted under 35 U.S.C. 154(b) by 702 days.

(21) Appl. No.: 14/548,413

(22) Filed: Nov. 20, 2014

(65) Prior Publication Data
US 2015/0150567 A1   Jun. 4, 2015

(30) Foreign Application Priority Data
Nov. 22, 2013   (JP) .................................. 2013-241762

(51) Int. Cl.
*A61B 17/17*    (2006.01)

(52) U.S. Cl.
CPC ...... *A61B 17/1764* (2013.01); *A61B 17/1714* (2013.01)

(58) Field of Classification Search
CPC ............................................... A61B 17/1764
See application file for complete search history.

(56) References Cited

U.S. PATENT DOCUMENTS

| 5,154,720 A | 10/1992 | Trott et al. | |
|---|---|---|---|
| 5,681,320 A * | 10/1997 | McGuire | A61B 17/0401 606/104 |
| 5,968,050 A * | 10/1999 | Torrie | A61B 17/1714 606/102 |

(Continued)

FOREIGN PATENT DOCUMENTS

| JP | 05-018511 | 3/1993 |
|---|---|---|
| JP | 05-277129 | 10/1993 |

(Continued)

OTHER PUBLICATIONS

Japanese Notification of Reasons for Refusal, issued on May 25, 2015, in corresponding Japanese Appln. No. 2013-241762, and English translation thereof.

*Primary Examiner* — Andrew Yang
(74) *Attorney, Agent, or Firm* — Wenderoth, Lind & Ponack, L.L.P.

(57) ABSTRACT

A guide pin piercing jig includes a cylinder unit and a frame having a positioning projection at a tip thereof, in which the cylinder unit has plural parallel guide pin insertion cylinders and tentative fixing unit and is attached to the frame slidably so as to be directed to the tip of the frame. It becomes possible to pierce living body bone with plural guide pins for hollow drills to a proper portion of a living body bone in a proper direction with parallel arrangement to form a bone tunnel that has a rectangular or elliptical opening and is suitable for tendon transplantation.

6 Claims, 19 Drawing Sheets

(56) References Cited

U.S. PATENT DOCUMENTS

| | | | |
|---|---|---|---|
| 6,120,511 A | 9/2000 | Chan | |
| 9,468,449 B2 * | 10/2016 | Smith | ............... A61B 17/1714 |
| 2003/0216742 A1 | 11/2003 | Wetzler et al. | |
| 2008/0103506 A1 | 5/2008 | Volpi et al. | |
| 2012/0109136 A1 | 5/2012 | Bourque et al. | |
| 2013/0023891 A1 | 1/2013 | Berberich et al. | |
| 2013/0030442 A1 | 1/2013 | Pilgeram et al. | |
| 2013/0053959 A1 | 2/2013 | Lizardi et al. | |

FOREIGN PATENT DOCUMENTS

| | | |
|---|---|---|
| JP | 5-95507 | 12/1993 |
| JP | 2001-525210 | 12/2001 |
| JP | 2008-132324 | 6/2008 |
| JP | 2013-043093 | 3/2013 |
| WO | 99/29237 | 6/1999 |
| WO | 2012/122497 | 9/2012 |

* cited by examiner

JIG FOR GUIDE PIN PIERCING

BACKGROUND OF THE INVENTION

1. Technical Field

The present invention relates to a jig to be used for piercing a living body bone with a guide pin for a boring hollow drill. More specifically, the present invention relates to a guide pin piercing jig which is used for piercing a bone of the knee joint or the like with a guide pin for a hollow drill, for example, in reconstruction of a torn anterior cruciate ligament, correctly at the position and direction according to the intention of a doctor in boring, through the bone of the knee joint or the like, by the hollow drill, a bone tunnel that is necessary to transplant a tendon acquired from another part in the knee joint or the like.

2. Description of the Related Art

As is well known, in reconstruction of a torn anterior cruciate ligament (ACL), it is necessary to bore, through a bone of the knee joint at a proper location, a bone tunnel that is necessary to transplant a tendon acquired from another part in the knee joint.

As a device used for such ACL reconstruction, proposed is a device for determining a position of a second bone tunnel to be bored through a shinbone top portion of the knee joint on the basis of a first bone tunnel that has been bored through a thighbone bottom portion of the knee joint (JP-A-2009-195701).

This device includes: a long and narrow main body having a near end and a far end; an arm which extends from the far end of the main body at a certain angle; a spherical tip portion formed at a far end of the arm; and an outrigger provided at the near end of the main body, and the device is configured to permit the following operation. When the spherical tip portion of the device is inserted into a first bone tunnel that has been bored through a thighbone bottom portion of the knee joint and serves as a reference, the arm indicates a proper position and angle of a second bone tunnel to be bored through a shinbone top portion. A second bone tunnel can be formed at a proper angle at a proper position of the shinbone top portion by boring it by a hollow drill along a guide wire that is stuck into the shinbone top portion from a wire insertion cylinder of the outrigger.

SUMMARY OF THE INVENTION

In the device of JP-A-2009-195701, as described above, when a reference first bone tunnel is bored through a thighbone bottom portion of the knee joint, a proper position and angle of a second bone tunnel to be bored through a shinbone top portion of the knee joint can be determined by inserting the spherical tip portion into the first bone tunnel. However, this device has a problem that a proper position and angle of a second bone tunnel to be bored through a shinbone top portion cannot be determined in the case where no first bone tunnel is bored through a thighbone bottom portion of the knee joint.

The device of Patent document 1 has another problem. That is, since a second bone tunnel is bored through a shinbone top portion by a hollow drill by sticking one guide pin into the shinbone top portion, the second bone tunnel is formed so as to have a circular opening, and it is not possible to form a bone tunnel having a rectangular or elliptical opening which allow an approximately rectangular-parallelepiped-shaped bone piece, located at one end, of an transplantation tendon to be inserted into it stably and fixed to the shinbone top portion strongly with fixing screws and which is suitable for tendon transplantation.

The present invention has been made in the above circumstances, and an object of the present invention is therefore to provide a guide pin piercing jig which make it possible to pierce a living body bone with plural parallel guide pins for hollow drills to a proper portion in a proper direction even if no reference bone tunnel is bored, to thereby make it possible to bore plural bone tunnels through the living body bone by the hollow drills that are guided by the respective guide pins inserted therein and to form a bone tunnel that has a rectangular or elliptical opening and hence is suitable for tendon transplantation by boring a link tunnel that connects the plural bone tunnels and subjecting it to chiseling or the like.

To attain the above object, a guide pin piercing jig according to a present invention is a guide pin piercing jig for piercing a living body bone with guide pins for boring hollow drills in such a manner as to determine positions and a direction of the guide pins, which includes:

a frame having a positioning projection at a tip thereof; and a cylinder unit, in which the cylinder unit has a plurality of parallel guide pin insertion cylinders and a tentative fixing unit and is attached to the frame slidably so as to be directed to the tip of the frame.

In a guide pin piercing jig according to the present invention, it is desirable that:

an angle at which a center line of an inside surface of a tip arm of the frame and center lines of the guide pin insertion cylinders cross each other is in a range of 60° to 90°;

a boring aiming portion in a vicinity of the positioning projection provided at the tip of the frame is included;

a surface, to be brought into contact with a living body bone, of the boring aiming portion is inclined from a center line of an inside surface of a tip arm of the frame by 5° to 30°;

the cylinder unit is detachable from the frame;

the cylinder unit is configured to integrate the plural parallel guide pin insertion cylinders with each other;

a tip of the cylinder unit is inclined from a center line thereof by 30° to 80°;

a length of a tip arm of the frame is in a range of 10 to 50 mm; and the frame has a bent portion which is located at a position that is distant from the tip of the frame by 10 to 50 mm and bent at 30° to 80°, and a tip arm which extends straightly from the bent portion to the tip of the frame is formed.

The guide pin piercing jig according to invention makes it possible to pierce a living body bone with plural guide pins in a proper direction to a proper portion of the living body bone with a parallel arrangement according to the intention of a doctor, by: positioning the tip of the frame by sticking the projection of the tip of the frame to a proper portion of the living body bone through which to bore a bone tunnel; tentatively fixing the tips of the plural parallel guide pin insertion cylinders of the cylinder unit to the living body bone by sliding the guide pin insertion cylinders toward the tip of the frame; and, in this state, piercing the living body bone with plural guide pins for hollow drills by inserting them into the respective guide pin insertion cylinders from their rear ends until they reach the tip of the frame. In the next step, the guide pins are inserted into the respective hollow drills and the living body bone is bored by the guided hollow drills, whereby plural penetration bone tunnels can be formed parallel with each other to a proper portion of the living body bone in a proper direction. As described later, in the further next step, the two bone tunnels are connected to each other by boring a tunnel between them by a center drill and a connected bone tunnel is subjected to chiseling into a rectangular or elliptical shape or expansion with a dilator, whereby a bone tunnel having a rectangular or elliptical opening which is different from an existing circuit bone tunnel and suitable for tendon transplantation can be formed through the living body bone to a proper portion in a proper direction.

As described above, the guide pin piercing jig according to invention makes it possible to pierce a living body bone with plural guide pins to a proper portion of the living body bone in a proper direction with a parallel arrangement according to the intention of a doctor. For example, in a case of boring bone tunnels for tendon transplantation through a shinbone top portion of the knee joint in ACL reconstruction, plural guide pins can pierce the shinbone top portion through which to bore a bone tunnel to a proper portion in a proper direction with parallel arrangement by inserting tip portions of the frame into the knee joint from the front side, positioning the tip of the frame by sticking a tip positioning projection of the frame into a proper portion, to which to bore a bone tunnel, of a shinbone top surface, and piercing the shinbone top portion with the plural guide pins from the plural guide pin insertion cylinders toward the tip of the frame in the same manner as described above. Therefore, by boring the shinbone top portion by hollow drills along the respective guide pins, plural bone tunnels that penetrate through the shinbone top portion from its front surface to its proper portion can be formed in a proper direction. In subsequent steps, the plural bone tunnels are connected to each other by boring a tunnel between them and a connected bone tunnel is subjected chiseling or the like. As a result, a bone tunnel that has a rectangular or elliptical opening and hence is suitable for tendon transplantation can be formed through the shinbone top portion to a proper portion in a proper direction.

In a guide pin piercing jig according to the invention in which the angle at which the center line of the inside surface of the tip arm of the frame and the center lines of the guide pin insertion cylinders cross each other is in the range of 60° to 90°, the length of the tip arm of the frame is in the range of 10 to 50 mm, the frame has the bent portion which is located at a position that is distant from the tip of the frame by 10 to 50 mm and bent at 30° to 80°, and the tip arm extends straightly from the bent portion to the tip of the frame, is high in jig operability (easy to handle). In particular, it is suitable to pierce a shinbone top portion of the knee joint with guide pins for hollow drills to bore a bone tunnel for tendon transplantation through the shinbone top portion in ACL reconstruction, and makes it possible to easily pierce a shinbone top portion with guide pins at proper positions in a proper direction according to the intension of a doctor.

In a guide pin piercing jig according to the invention in which the boring aiming portion is provided in the vicinity of the positioning projection which is provided at the tip of the frame, it is possible to pierce a living body bone with plural guide pins by determining, clearly in a specific manner, a proper portion to which to form a bone tunnel using the boring aiming portion by bringing the boring aiming portion into contact with the living body bone and positioning it by means of the positioning projection. In particular, the guide pin piercing jig in which the surface, to be brought into contact with a living body bone, of the boring aiming portion is inclined from the center line of the inside surface of the tip arm of the frame by 5° to 30° is very high in operability in ACL reconstruction because when the tip arm is inserted into the knee joint this surface of the boring aiming portion can stably be brought into contact with a portion to which to form a bone tunnel, so as to conform to a shinbone top surface.

In a guide pin piercing jig according to the invention in which the tip of the cylinder unit is inclined from its center line by 30° to 80°, in ACL reconstruction the tip of the cylinder unit can be fixed to a shinbone top portion tentatively by means of the tentative fixing unit so as to conform to a front surface of the shinbone top portion stably.

A guide pin piercing jig according to the invention in which the cylinder unit can be detached from the frame can be carried easily in a state that the frame is separated from the cylinder unit and can be assembled easily and used at a medical treatment site. Furthermore, in the guide pin piercing jig in which the cylinder unit is configured in such a manner that the plural parallel guide pin insertion cylinders are integral with each other, the number of components is reduced and work of attaching or detaching the cylinder unit to or from the frame can be carried out more easily.

DETAILED DESCRIPTION OF THE INVENTION

Guide pin piercing jigs according to embodiments of the present invention will be hereinafter described in detail with reference to the drawings.

Figure 1:
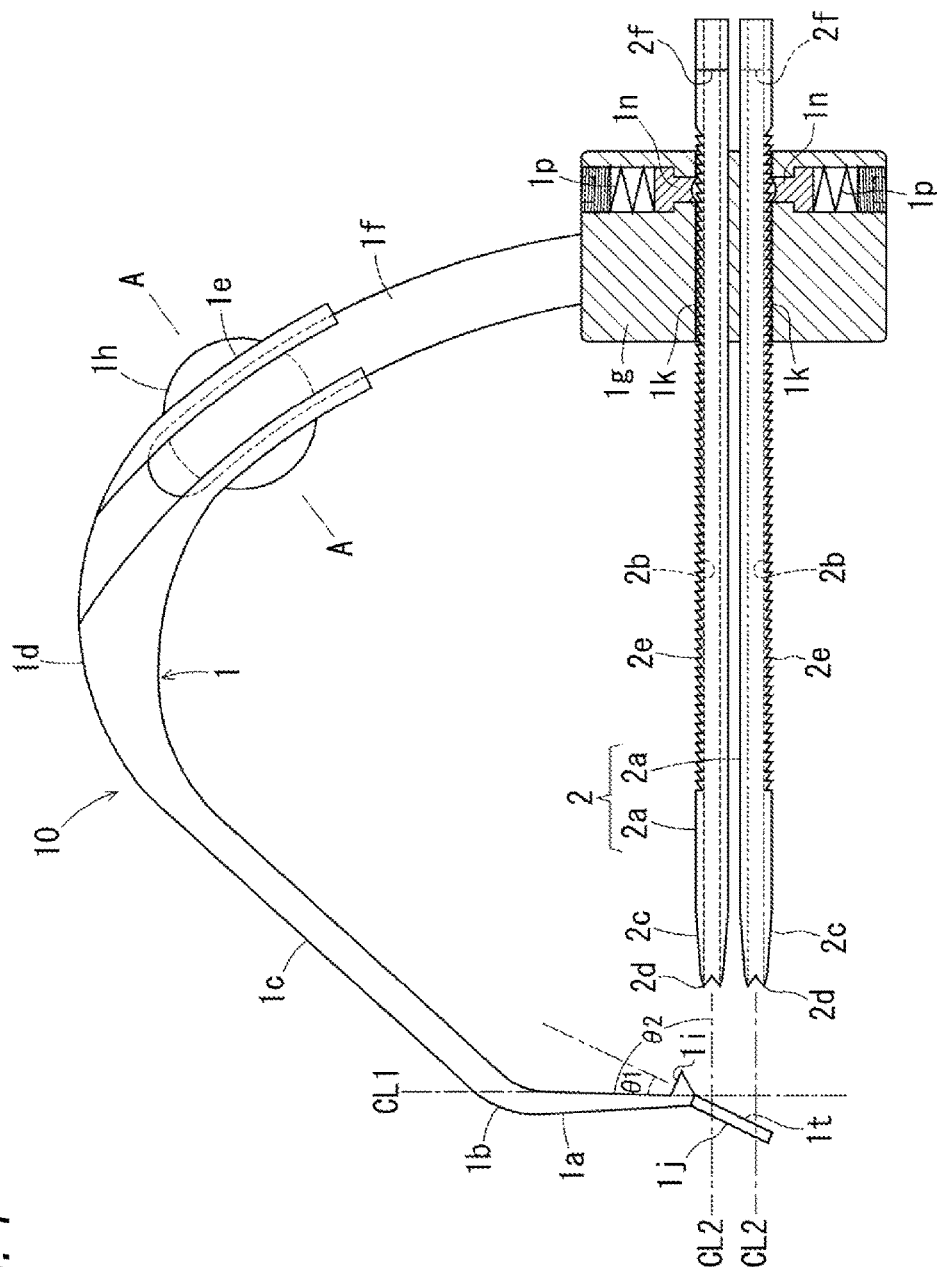
FIG. 1 is a partially sectional side view of a guide pin piercing jig according to an embodiment of the present invention.
Figure 2:
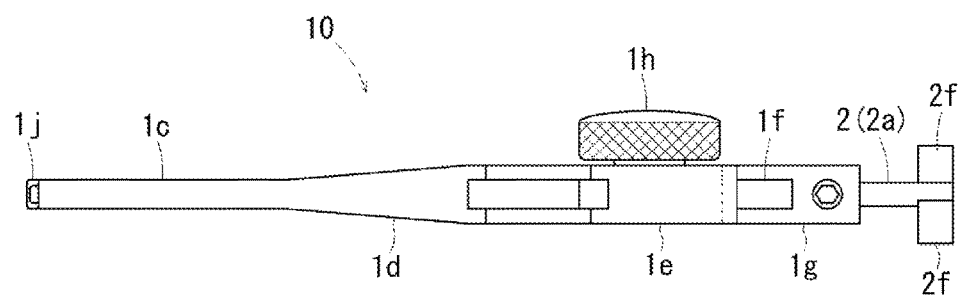
FIG. 2 is a plan view of the guide pin piercing jig.
Figure 3:
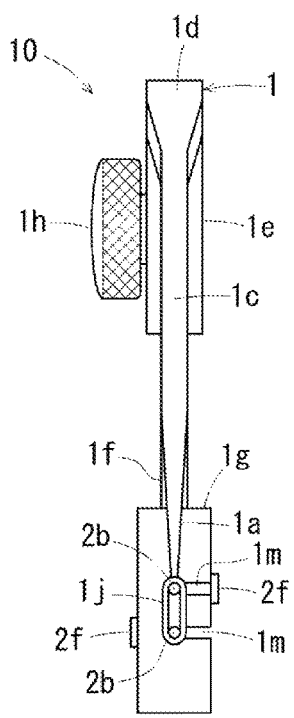
FIG. 3 is a front view of the guide pin piercing jig.
Figure 4:
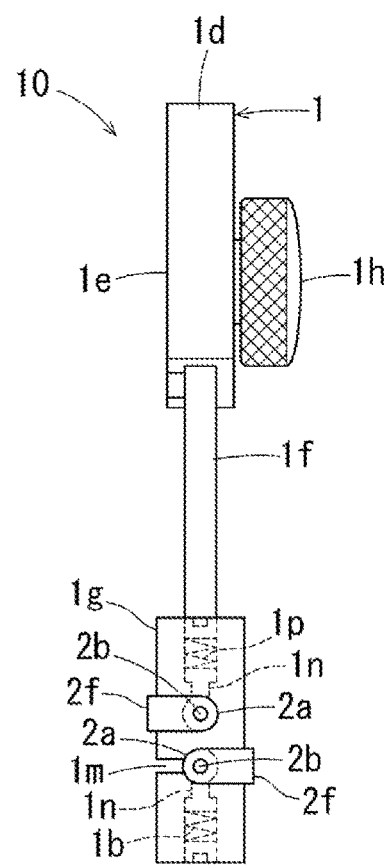
FIG. 4 is a rear view of the guide pin piercing jig.
Figure 5:
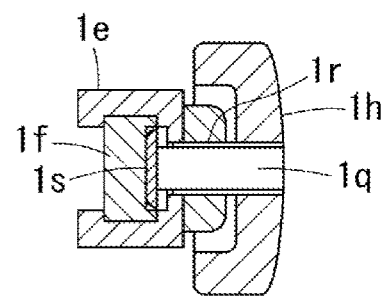
FIG. 5 is an end view of cutting FIG. 1 along the line A-A.
Figure 6:
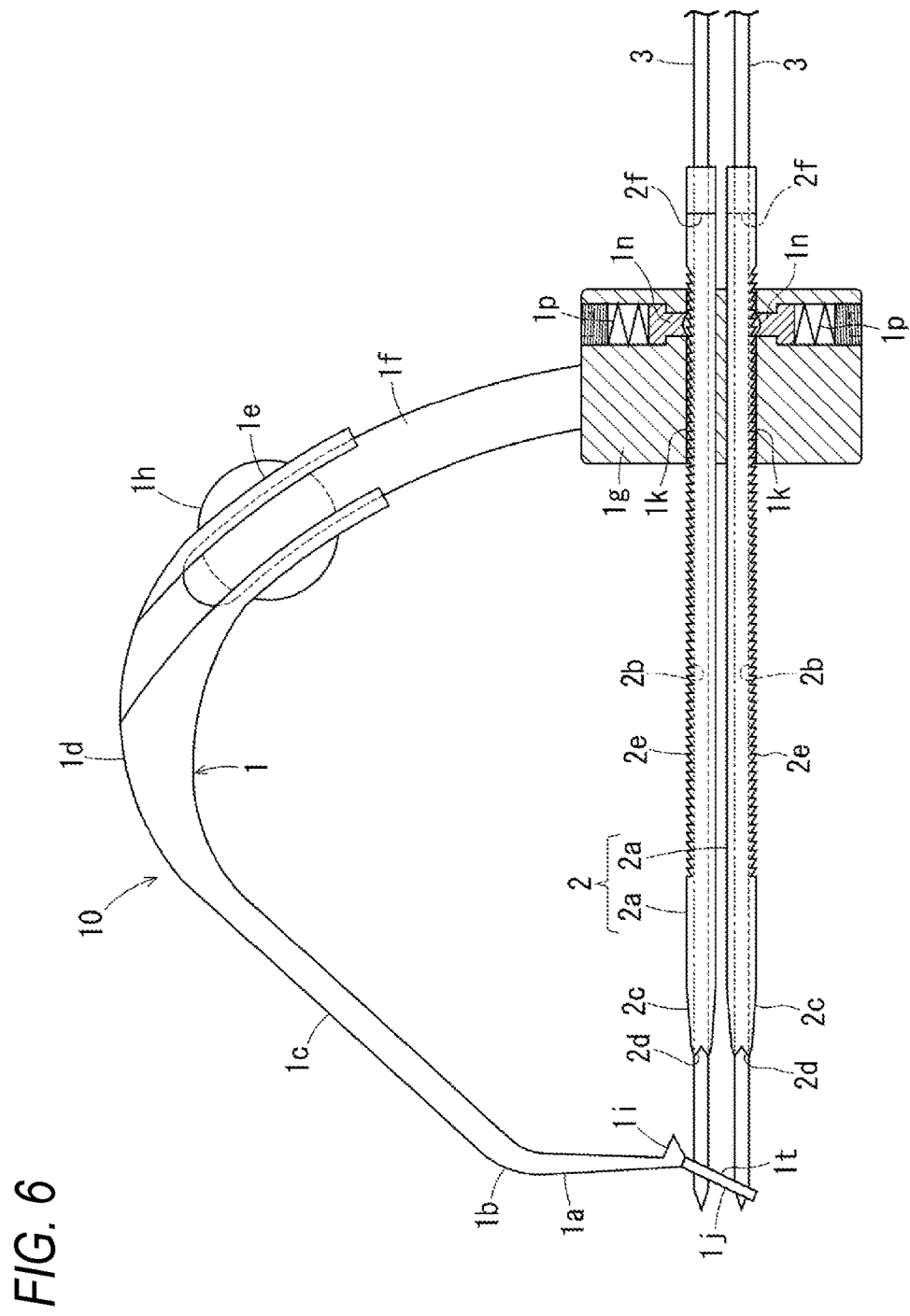
FIG. 6 is a partially sectional side of the guide pin piercing jig in which guide pins are inserted in plural respective guide pin insertion cylinders.
Figure 7:
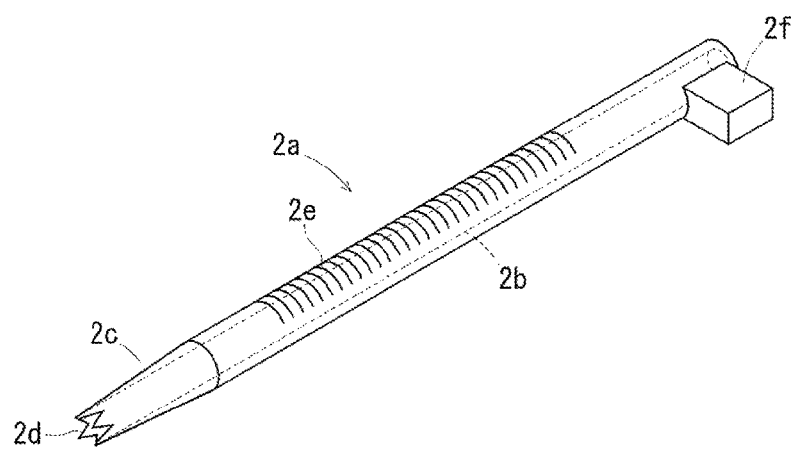
FIG. 7 is a perspective view of one guide pin insertion cylinder.
Figure 8:
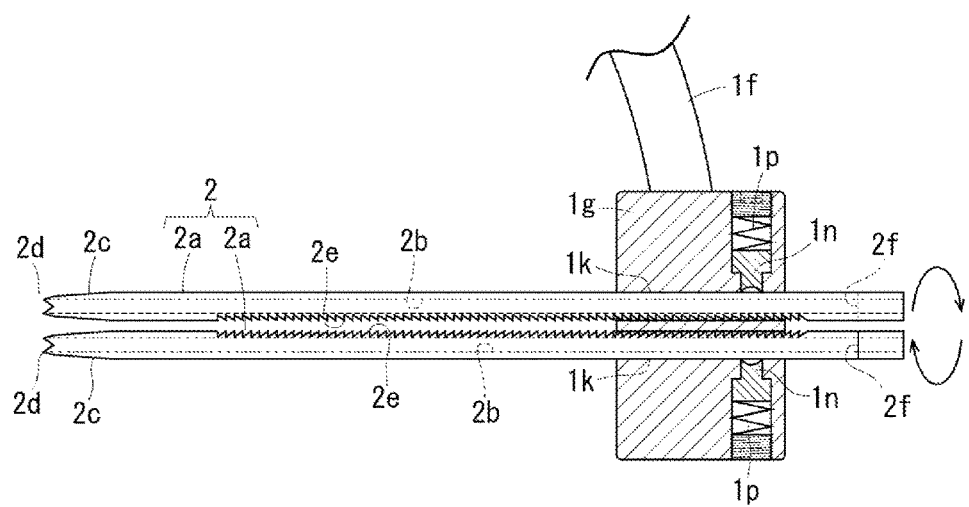
FIG. 8 is a sectional view of part of the guide pin piercing jig and shows a state that the guide pin insertion cylinders are unlocked and are thereby made slidable rearward.

FIG. 1 is a partially sectional side view of a guide pin piercing jig according to an embodiment of the invention, FIG. 2 is a plan view of the guide pin piercing jig, FIG. 3 is a front view of the guide pin piercing jig, FIG. 4 is a rear view of the guide pin piercing jig, FIG. 5 is an end view of cutting FIG. 1 along the line A-A, FIG. 6 is a partially sectional side of the guide pin piercing jig in which guide pins are inserted in plural respective guide pin insertion cylinders, FIG. 7 is a perspective view of one guide pin insertion cylinder, and FIG. 8 is a sectional view of part of the guide pin piercing jig and shows a state that the guide pin insertion cylinders are unlocked and are thereby made slidable rearward.

As described later, the guide pin piercing jig 10 shown in FIGS. 1-5 is to be used for piercing a shinbone top portion of the knee joint with guide pins for guidance of hollow drills in such a manner that their positions and direction are determined correctly according to the intension of a doctor in boring, in the shinbone top portion, by the hollow drills, bone tunnels that are necessary to transplant a tendon acquired from another part in the knee joint in reconstruction of a torn anterior cruciate ligament (ACL). The guide pin piercing jig 10 includes a frame 1 and a cylinder unit 2 which are made of a metal such as titanium or stainless steel.

The frame 1 includes a straight tip arm 1a, a bent portion 1b which is connected to the front end of the tip arm 1a, a straight intermediate arm 1c which is connected to the bent portion 1b, a convex-curved portion 1d which is connected to the intermediate arm 1c, an arc-shaped sheath 1e which is connected to the convex-curved portion 1d, an arc-shaped plate 1f which is inserted in the arc-shaped sheath 1e slidably, a cylinder unit attachment portion 1g which is connected to the rear end of the arc-shaped plate 1f, and a rotary knob 1h for locking the arc-shaped plate 1f to stop its slide. A sharp positioning projection 1i which is triangular when viewed from the side projects from the tip of the frame 1 toward the inside of the frame 1. A boring aiming portion 1j is provided at the tip of the frame 1 in the vicinity of the positioning projection 1i.

The cylinder unit 2 includes plural guide pin insertion cylinders 2a, 2a which are inserted in plural parallel insertion holes 1k, 1k formed in the rear-end attachment portion 1g of the frame 1, respectively, and attached to it parallel with each other so as to be arranged vertically and directed to the boring aiming portion 1j.

The term "vertically" means that they are arranged in the top-bottom direction in a side view of the guide pin piercing jig 10 (see FIG. 1).

The tip boring aiming portion 1j of the frame 1 is a ring-shaped body having an elliptical opening (see FIG. 3), and the center lines CL2, CL2 of the plural respective guide pin insertion cylinders 2a, 2a pass through the opening of the boring aiming portion 1j (see FIG. 1). Therefore, as shown in FIG. 6, when plural guide pins 3, 3 are inserted into the respective guide pin insertion cylinders 2a, 2a from behind, the tips of the guide pins 3, 3 go into the opening of the boring aiming portion 1j.

The reason why as mentioned above the boring aiming portion 1j is made a ring-shaped body having an elliptical opening that approximately coincides with an opening shape (rectangular or elliptical (mentioned above)) of a bone tunnel that is suitable for tendon transplantation and is to be formed finally is to allow a doctor to image a bone tunnel that is suitable for tendon transplantation when the boring aiming portion 1j is applied to a proper location of a living body bone through which to bore a bone tunnel.

As shown in FIG. 1, the boring aiming portion 1j projects obliquely downward from the tip of the tip arm 1a of the frame 1. A back surface 1t, to be brought into contact with a living body bone, of the boring aiming portion 1j is inclined by an angle θ1, specifically 5° to 30° (in the embodiment, about 15°), with respect to the center line CL1 of the inside surface of the tip arm 1a and is perpendicular to the paper surface of FIG. 1. That is, with the y axis, x axis, and z axis defined in FIG. 1 as the center line CL1 of the inside surface of the tip arm 1a, the axis perpendicular to the center axis CL1 in the paper surface, and the axis perpendicular to the paper surface, respectively, the tip surface 1t is parallel with the z axis whereas being inclined by concretely 5° to 30° (in the embodiment, about 15°) from the y axis. Since the surface 1t (hereinafter referred to as a contact surface it), to be brought into contact with a living body bone, of the boring aiming portion 1j is inclined by 5° to 30°, when as described later the tip arm 1a is inserted into the knee joint in ACL reconstruction, the contact surface 1t of the boring aiming portion 1j can stably be brought into contact with a proper portion to which to form a bone tunnel so as to conform to a shinbone top surface. This provides an advantage that the operability of the guide pin piercing jig 10 is enhanced.

The "inside surface" of the tip arm 1a means the surface of the tip arm 1a that is directed to the inside of the frame 1.

As shown in FIG. 1, the tip arm 1a of the frame 1 is a straight, prism-shaped portion that becomes narrower as the position comes closer to the tip. It is desirable that its length is about 10 to 50 mm; in the embodiment, the length is set at about 25 mm The bent portion 1b of the frame 1 is a bent portion configured to be connected to the tip arm 1a, to be distant from the tip of the frame 1 by 10 to 50 mm, and to be bent by 30° to 80°, which is about 40° in the embodiment.

The intermediate arm 1c that is connected to the bent portion 1b is a straight, prism-shaped portion. It is desirable that its length be about 50 to 100 mm; in the embodiment, the length is set at about 70 mm The arc-shaped center lines of the arc-shaped sheath 1e (a sheath whose one side wall is formed with a slit) which is connected to the intermediate arm 1c via the convex-curved portion 1d and the arc-shaped plate 1f which is inserted in the arc-shaped sheath 1e slidably have the same radius of curvature, and the center of their imaginary circle is located approximately at the position of the boring aiming portion 1j which is provided at the tip of the arm 1. That is, the radius of curvature of the arc-shaped center lines of the arc-shaped sheath 1e and the arc-shaped plate 1f is approximately equal to the dimension from the boring aiming portion 1j which is provided at the tip of the arm 1 to the arc-shaped center lines. So that the frame 1 can stride over a shinbone top portion of the knee joint, the radius of curvature is set at 80 to 200 mm, desirably 100 to 150 mm; in the embodiment, the radius of curvature is set at about 125 mm As shown in FIG. 5, a screw shaft 1q of the rotary knob 1h is threadedly engaged with a screw hole 1r which is formed through a side wall (located on the side opposite to a side wall in which the slit is formed) of the arc-shaped sheath 1e. When the screw shaft 1q is screwed in by rotating the rotary knob 1h with fingers, a tip contact piece is of the screw shaft 1q comes into pressure contact with the bottom surface of a shallow recess that is formed in a side surface of the arc-shaped plate 1f, whereby the arc-shaped plate 1f is fixed, that is, made incapable of sliding. Therefore, the entire arc length of the frame 1 can be adjusted by sliding the arc-shaped plate 1f in the arc-shaped sheath 1e along the circular arc with the rotary knob 1h loosened and then fixing the arc-shaped plate 1f to making it incapable of sliding by rotating the rotary knob 1h. In this manner, as shown in FIG. 1, the crossing angle θ2 between the center line CL1 of the tip arm 1a of the frame 1 and the center line CL2 of each guide pin insertion cylinder 2a can be set in a range of 60° to 90°.

Even if as described above the angle θ2 is varied in the range of 60° to 90°, since the center of the imaginary circle of the arc-shaped sheath 1e and the arc-shaped plate 1f coincides with the tip boring aiming portion 1j of the frame 1, the center lines CL2 of the plural guide pin insertion cylinders 2a, 2a (in other words, guide pins 3, 3 inserted in the respective guide pin insertion cylinders 2a, 2a) necessarily pass through the boring aiming portion 1j. Therefore, the guide pins 3, 3 can correctly pierce a living body bone to which the boring aiming portion 1j is applied, to a portion to which to bore a bone tunnel.

In ACL reconstruction, ranges of the angle θ2 that are smaller than 60° or larger than 90° are not desirable because it is difficult to pierce a shinbone top portion with guide pins 3, 3 obliquely upward from its front surface to its top surface.

As described above, the guide pin piercing jig 10 is configured in the following manners. The crossing angle θ2 between the center line CL1 of the inside surface of the tip arm 1a of the frame 1 and the center line CL2 of each guide pin insertion cylinder 2a is set in the range of 60° to 90°. As described before, the length of the tip arm 1a is set at 10 to 50 mm, the bent portion 1b which is bent at 30° to 80° is provided so as to be distant from the tip of the frame 1 by 10 to 50 mm, and the radius of curvature of the arc-shaped center lines of the arc-shaped sheath 1e and the arc-shaped plate 1f is set to 80 to 200 mm, desirably 100 to 150 mm. The thus-configured guide pin piercing jig 10 is very high in operability (very easy to handle). In particular, the guide pin piercing jig 10 is suitable for a case of piercing a shinbone top portion of the knee joint with guide pins 3 to bore a bone tunnel for tendon transplantation through the shinbone top portion in ACL reconstruction as described later. It becomes possible to pierce the shinbone top portion with guide pins 3 easily at proper positions intended by a doctor and in a direction also intended by the doctor.

As shown in FIGS. 1, 7, and 8, a straight cylinder hole 2b through which to insert a guide pin is formed through each of the plural guide pin insertion cylinders 2a, 2a of the cylinder unit 2 which is attached to the rear-end attachment portion 1g of the frame 1, so as to share the center axis CL2. Whereas each straight cylinder hole 2b has a straight cylinder shape as a whole, a tip neighborhood portion 2c is tapered and its tip is formed with a sharp opening 2d (tentative fixing unit) having cuts. A top portion, having a width that is approximately equal to ¼ of the circumference, of the circumferential surface of a central portion of each guide pin insertion cylinder 2a excluding its portions adjacent to its front end and rear end is formed with a sawtooth-shaped ratchet portion 2e which extends continuously in the longitudinal direction of the guide pin insertion cylinder 2a. Furthermore, a projection piece 2f projects sideways from a rear end portion of each guide pin insertion cylinder 2a.

On the other hand, as shown in FIGS. 1 and 8, plural insertion holes 1k, 1k (insertion holes each of which is formed with a slit 1m on one side as shown in FIG. 3) for slidable attachment of the plural respective guide pin insertion cylinders 2a, 2a are formed through the rear-end attachment portion 1g of the frame 1 parallel with each other so as to be arranged vertical (in the top-bottom direction). A pair of (top an bottom) engagement projections 1n, 1n for preventing rearward slides of the guide pin insertion cylinders 2a, 2a by engaging with their ratchet portions 2e, 2e project slightly, being pushed by compression springs 1p, 1p from above and below, through a top opening formed in the inner surface that defines the top insertion hole 1k and a bottom opening formed in the inner surface that defines the bottom insertion hole 1k, respectively.

Therefore, as shown in FIG. 1, when the top guide pin insertion cylinder 2a is inserted into the top insertion hole 1k of the attachment portion 1g from behind with its ratchet portion 2e up and the bottom guide pin insertion cylinder 2a is inserted into the bottom insertion hole 1k of the attachment portion 1g from behind with its ratchet portion 2e down, the top engagement projection 1n is pushed up by the tapered surface of the tip portion 2c of the top guide pin insertion cylinder 2a and the bottom engagement projection 1n is pushed down by the tapered surface of the tip portion 2c of the bottom guide pin insertion cylinder 2a. The two guide pin insertion cylinders 2a, 2a are slid toward the tip boring aiming portion 1j of the frame 1 and the top and bottom engagement projections 1n, 1n are engaged with the ratchet portions 2e, 2e of the top and bottom guide pin insertion cylinders 2a, 2a from above and below being pushed by the compression springs 1p, 1p, to establish a state that rearward slides of the guide pin insertion cylinders 2a, 2a are prevented while being allowed to slide forward.

As shown in FIG. 8, the engagement between the engagement projections 1n, 1n and the ratchet portions 2e, 2e of the top and bottom guide pin insertion cylinder 2a is canceled by rotating the guide pin insertion cylinder 2a by 180° each (i.e., flipping them upside down) by rotating the projection pieces 2f, 2f. Therefore, the guide pin insertion cylinders 2a, 2a can be taken out of the rear-end attachment portion 1g of the frame 1 by sliding the two guide pin insertion cylinders 2a rearward in the above state.

Next, a method for using the above-described guide pin piercing jig 10 and a method for boring a bone tunnel is bored in knee joint ACL reconstruction will be described with reference to FIGS. 9-16.

Figure 9:
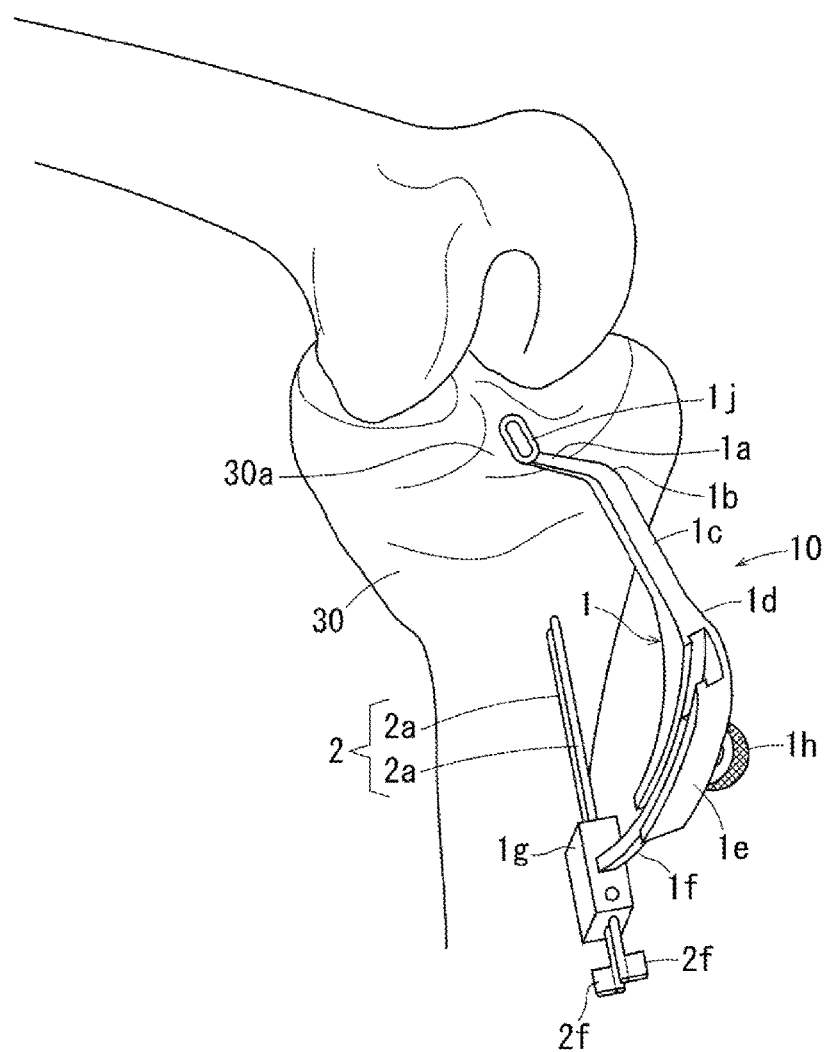
FIG. 9 illustrates an example manner of use of the guide pin piercing jig and shows a state that the tip of a frame is positioned by applying a boring aiming portion provided at the tip of the frame to a shinbone top surface of the knee joint and the tips of the plural guide pin insertion cylinders of a cylinder unit are fixed tentatively to a front surface of the shinbone top surface.

First, as shown in FIG. 9, the tip boring aiming portion 1j of the frame 1 of the guide pin piercing jig 10 is inserted into the knee joint from the front side. Then the contact surface 1t (unseen in FIG. 9) of the boring aiming portion 1j is applied to a recessed top surface 30a in a portion, to which to bore a bone tunnel, of a shinbone top portion 30 and is pressed against it strongly, whereby the positioning projection 1i (unseen in FIG. 9) of the frame 1 is stuck into the recessed top surface 30a of the shinbone top portion 30. Thus, the boring aiming portion 1j is positioned and fixed temporarily.

Since as mentioned above the boring aiming portion 1j is a ring-shaped body having an elliptical opening which approximately coincides with an opening shape (rectangular or elliptical) of a bone tunnel to be formed finally, a doctor can perform work of positioning the boring aiming portion 2b easily by applying the boring aiming portion 1j to a proper portion of the recessed top surface 30a of the shinbone top portion 30 while imaging the shape of a bone tunnel to be formed finally.

After completion of the work of positing the boring aiming portion 1j, as shown in FIG. 9 the plural guide pin insertion cylinders 2a, 2a that are attached to the rear-end attachment portion 1g of the frame 1 slid obliquely upward toward the front surface of the shinbone top portion 30 and their tip sharp openings 2d (unseen in FIG. 9) are stuck into the front surface of the shinbone top portion 30. Thus, the guide pin insertion cylinders 2a, 2a are fixed so as to extend in a proper direction that is intended by the doctor. When the guide pin insertion cylinders 2a, 2a are slid and their top openings are stuck in the above-described manner, as described above the engagement projections 1n, 1n which are exposed through the top openings formed in the inner surfaces of the insertion holes 1k, 1k of the attachment portion 1g are engaged with the ratchet portions 2e, 2e of the guide pin insertion cylinders 2a, 2a respectively. Therefore, the guide pin insertion cylinders 2a, 2a are locked to as to be incapable of being pulled out.

As described above, the direction (angle) of the guide pin insertion cylinders 2a, 2a is adjusted by adjusting the crossing angle θ2 between the center line CL1 of the inside surface of the tip arm 1a and the center lines CL2, CL2 of each guide pin insertion cylinders 2a, 2a in the range of 60° to 90° by changing the length by which the arc-shaped plate 1f is inserted in the arc-shaped sheath 1e by loosening the rotary knob 1h.

Figure 10:
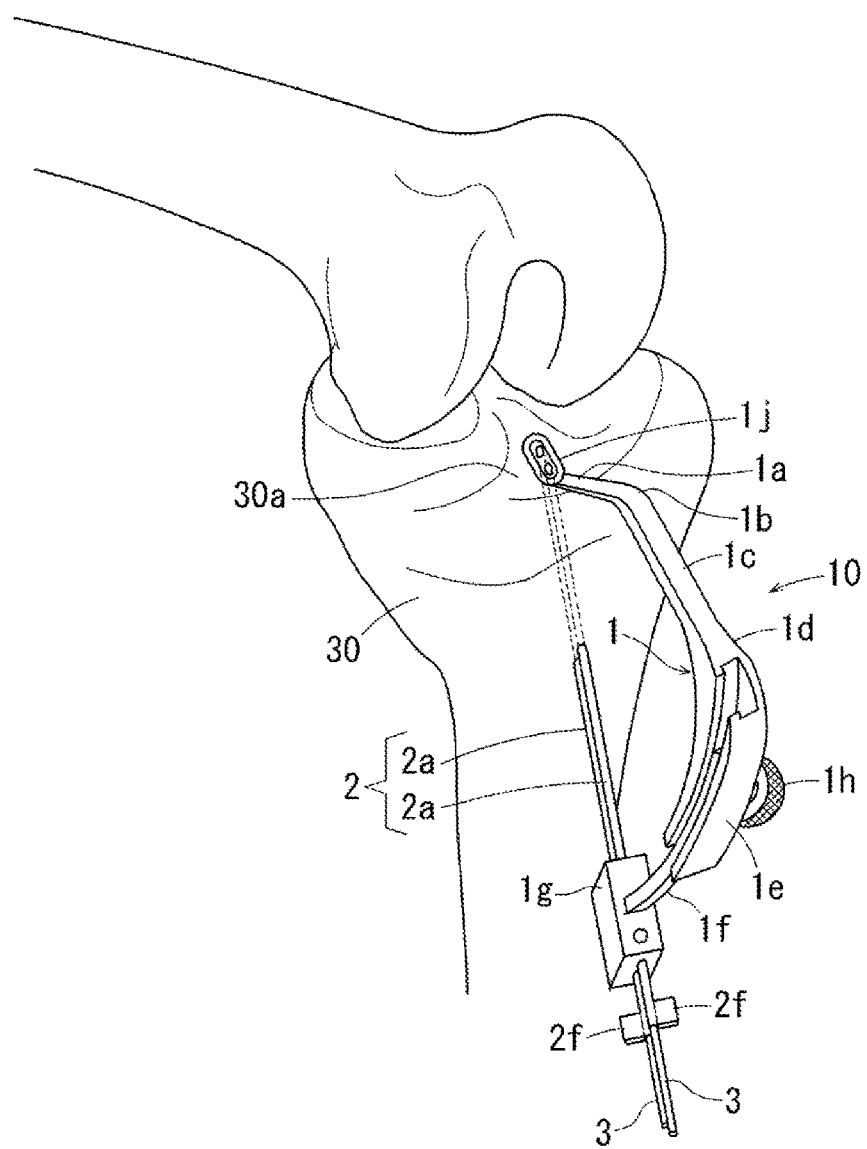
FIG. 10 illustrates the example manner of use of the guide pin piercing jig and shows a state that plural guide pins have been inserted into the plural respective guide pin insertion cylinders from their rear ends and have pierced the shinbone top portion until reaching the boring aiming portion provided at the tip of the frame.

Subsequently, as shown in FIG. 10, guide pins 3, 3 for hollow drills are inserted into the cylinder holes 2b, 2b (unseen in FIG. 10) of the guide pin insertion cylinders 2a, 2a and caused to pierce the shinbone top portion 30 until the tips of the guide pins 3, 3 go into the opening of the boring aiming portion 1j. The tips of the guide pins 3, 3 are sharp like the tip of a drill, and the guide pins 3, 3 can pierce the shinbone top portion 30 relatively easily when rotated. Whether or not the guide pins 3, 3 have penetrated through the shinbone top portion 30 and their tips have gone into the opening of the boring aiming portion 1j of the front cylinder unit 2 may be checked by inserting a fiber scope into the knee joint.

After confirmation of entrance of the tips of the guide pins 3, 3 into the boring aiming portion 1j, the guide pin insertion cylinders 2a, 2a are pulled out of the respective insertion holes 1k, 1k of the rear-end attachment portion 1g of the frame 1 and then removed from the respective guide pins 3, 3. Subsequently, the frame 1 is removed from the knee joint, as a result of which only the two guide pins 3, 3 are left as shown in FIG. 11 and the work of piercing the shinbone top portion 30 with the guide pins 3, 3 is completed.

How to pull the guide pin insertion cylinders 2a, 2a from the respective insertion holes 1k, 1k has already been described above and hence are not described here. Since as described above the side surface of the rear-end attachment portion 1g of the frame 1 is formed with the slits 1m, 1m (see FIG. 3), the frame 1 can be removed easily by removing the guide pins 3, 3 from the respective insertion holes 1k, 1k by moving the attachment portion 1g sideways and then pulling the frame 1 out of the knee joint by lifting up the tip of the frame 1.

In this operation, all the incised part to the living body is only four small openings for insertion of the tip portions (boring aiming portion 1j and tip arm 1a) of the frame 1, the plural guide pin insertion cylinders 2a, 2a the fiber scope, and a pipe to be used for filling the operation part with physiological saline. This operation method is superior because of a lighter load on the living body.

Figure 11:
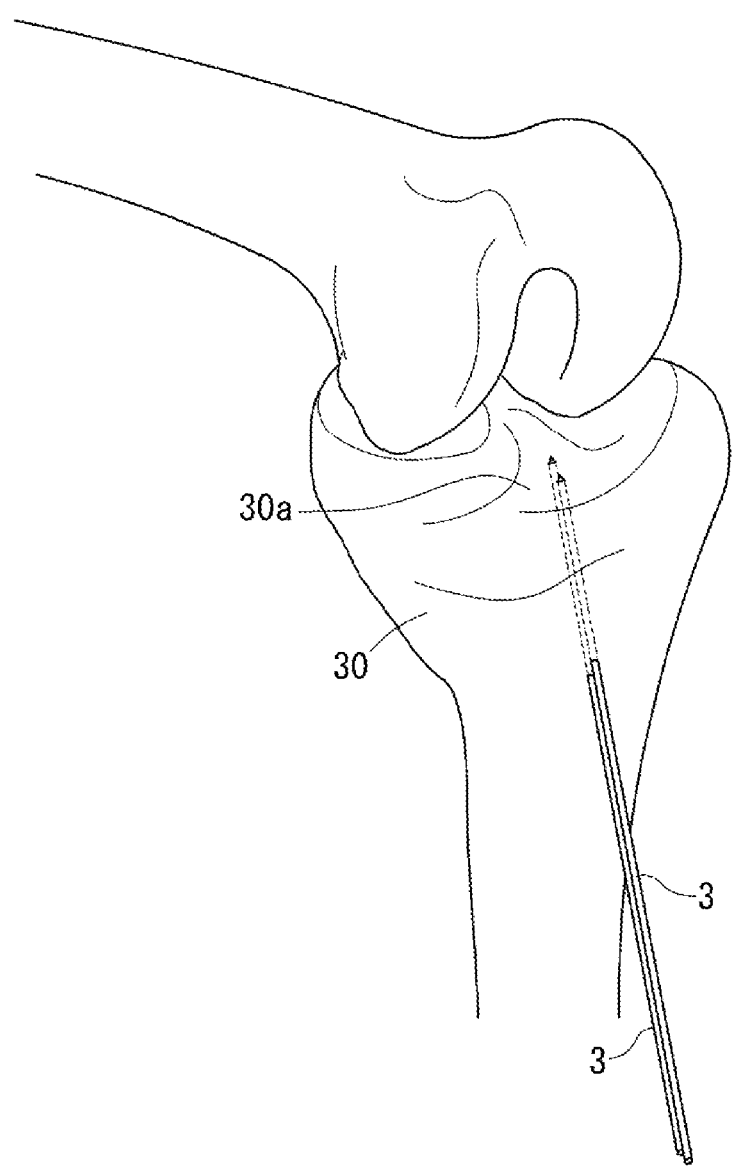
FIG. 11 illustrates the example manner of use of the guide pin piercing jig and shows a state that the plural guide pin insertion cylinders are pulled out and the frame is removed.
Figure 12:
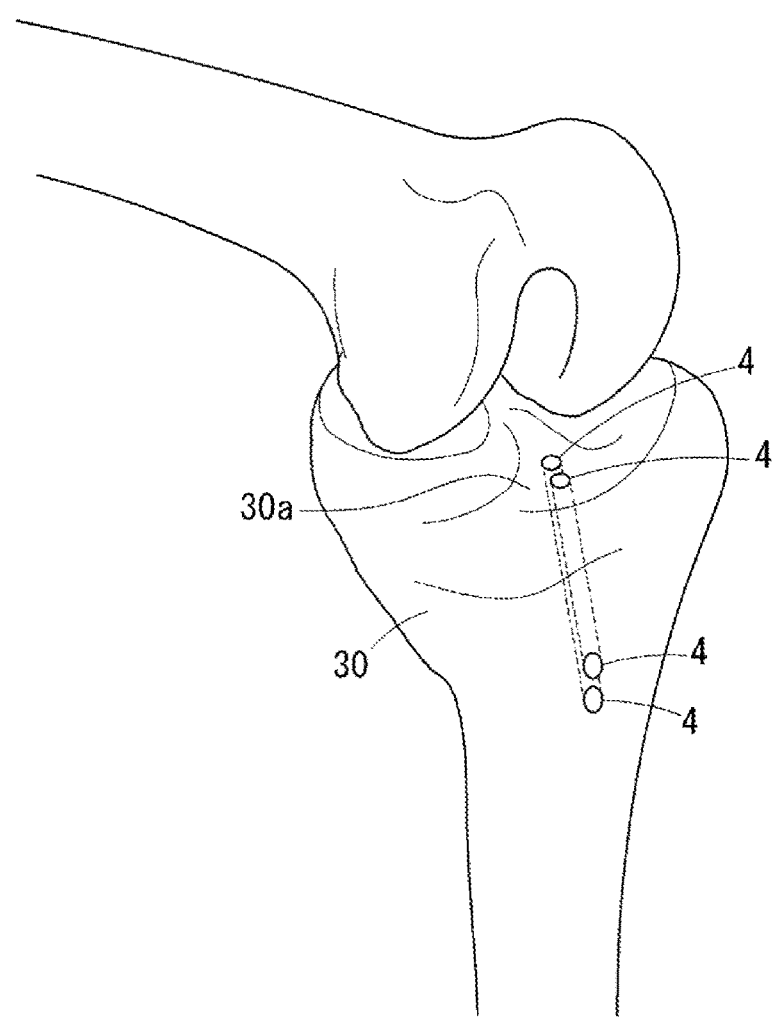
FIG. 12 is a perspective view showing the shinbone top portion of the knee joint in which plural bone tunnels are bored.

When the work of piercing the shinbone top portion 30 with the two guide pins 6 has been performed in the above-described manner using the guide pin piercing jig 10 according to the invention in the knee joint ACL reconstruction, as shown in FIG. 11 the two guide pins 3, 3 can pierce the shinbone top portion 30 in a proper direction intended by the doctor from the front surface of the shinbone top portion 30 to a proper portion of the recessed top surface 30a of the shinbone top portion 30 through which to bore a bone tunnel, so as to extend parallel with each other and to be arranged vertically. Therefore, by boring the shinbone top portion 30 along the guide pins 3, 3 by hollow drills (not shown), as shown in FIG. 12 two circular bone tunnels 4, 4 can be formed which penetrate through the shinbone top portion 30 in a proper direction from the front surface of the shinbone top portion 30 to a proper portion of the recessed top surface 30a, extend parallel with each other, and are arranged vertically.

Figure 13:
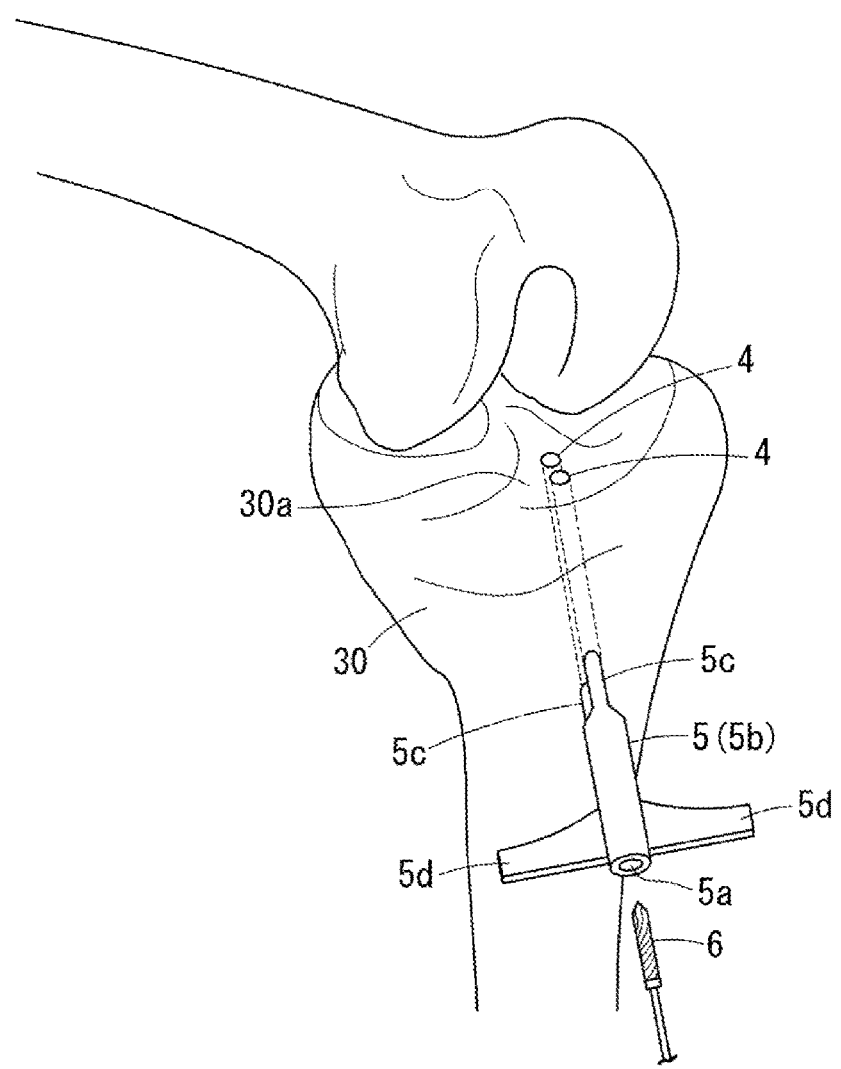
FIG. 13 is a perspective view showing a state that a center drill guide for guiding a center drill is inserted in the plural bone tunnels which are bored through the shinbone top portion of the knee joint.
Figure 14:
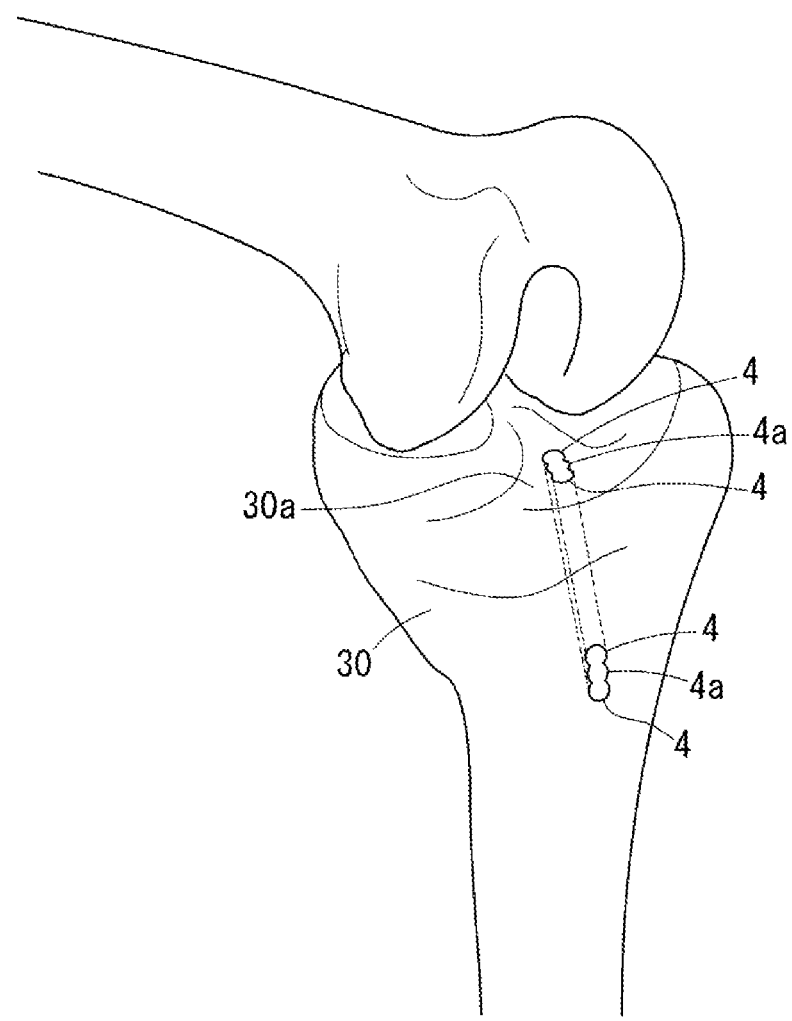
FIG. 14 is a perspective view showing the shinbone top portion of the knee joint in which the plural bone tunnels are connected to each other by boring a tunnel between them by the center drill.

In the next step, as shown in FIG. 13, two split cylinders 5c, 5c of a center drill guide 5 are inserted into the two respective bone tunnels 4, 4 of the shinbone top portion 30 from the side of its front surface and thereby attached to the shinbone top portion 30. Then a center drill 6 is inserted into a guide hole 5a of the center drill guide 5, whereby as shown in FIG. 14 a link tunnel 4a is formed between the two circular bone tunnels 4, 4 to link them.

As shown in FIGS. 17A, 17B, 17C, and 17D, the center drill guide 5 includes a large-diameter base cylinder 5b having a guide hole 5a through which to insert a center drill, the two small-diameter split cylinders 5c, 5c which project parallel with each other from the tip of the base cylinder 5b and are to be inserted into the bone tunnels 4, and a generally T-shaped grip portion 5d which is connected to the rear end of the base cylinder 5b. The split cylinders 5c are formed, along their center lines, with pin insertion holes 5e, 5e into which to insert the guide pins 3, 3, respectively. The pin insertion holes 5e, 5e extend parallel with the guide hole 5a of the base cylinder 5b at its two respective sides. To prevent interference with the center drill to be inserted through the guide hole 5a, slits are formed in confronting cylinder wall portions between the split cylinders 5c, 5c.

The thus-configured center drill guide 5 is used in the following manner. The two guide pins 3, 3 that are left inserted in the bone tunnels 4, 4 are inserted into the respective pin insertion holes 5e, 5e, the split cylinders 5c, 5c are slid and guided to the respective bone tunnels 4, 4, and the split cylinders 5c, 5c are inserted into the bone tunnels 4, 4 and fixed by gripping the grip portion 5*d* with a hand. A link tunnel 4*a* is formed between the two bone tunnels 4, 4 so as to connect them by the center drill 6 that is inserted through the guide hole 5*a*. Then the split cylinders 5*c*, 5*c* are pulled out of the bone tunnels 4 and the center drill guide 5 is removed.

Where the guide pins 3, 3 have been removed from the bone tunnels 4, 4, the tip split cylinders 5*c*, 5*c* are merely inserted into the respective bone tunnels 4, 4 and fixed by gripping the grip portion 5*d*. In this case, the pin insertion holes 5*e*, 5*e* are not necessary and hence need not always be formed.

Figure 15:
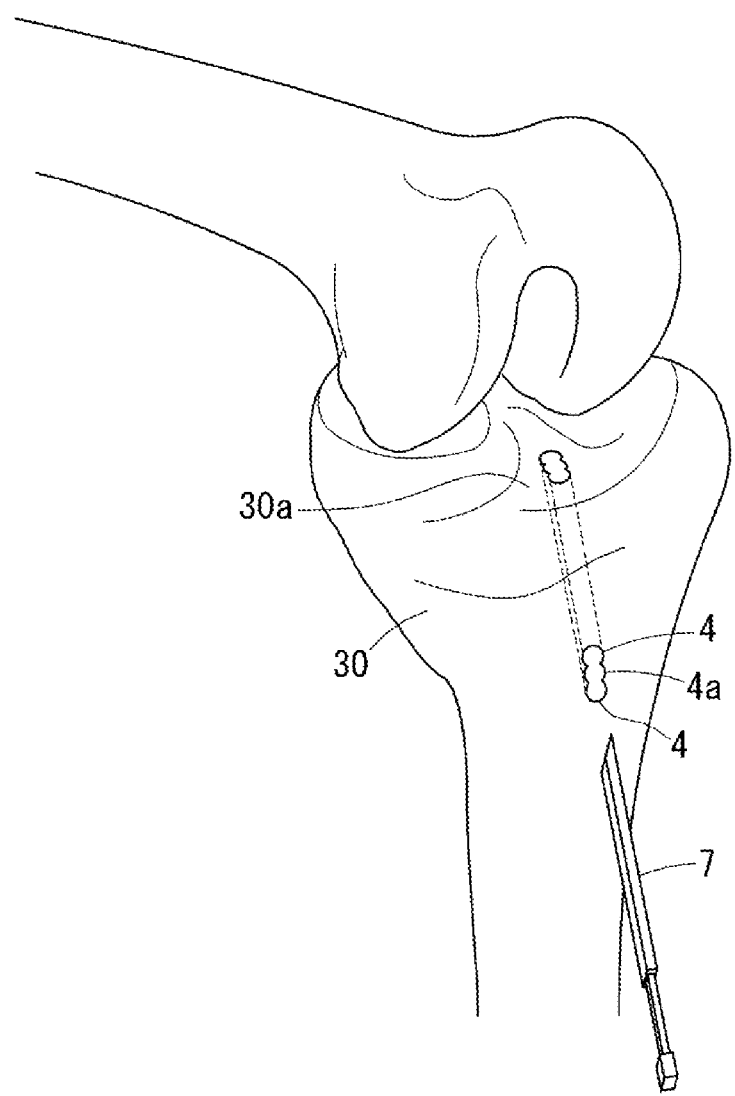
FIG. 15 is a perspective view showing how the continuous bone tunnel formed through the shinbone top portion of the knee joint are subjected to cutting with a chisel.
Figure 16:
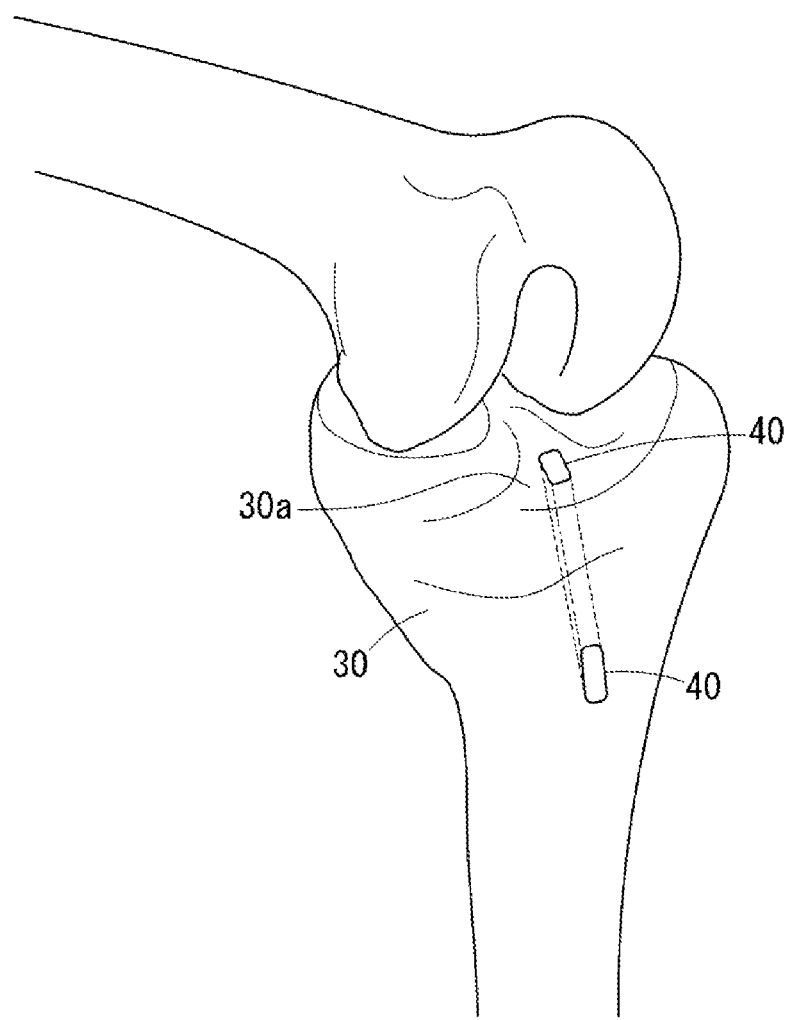
FIG. 16 is a perspective view showing the shinbone top portion of the knee joint through which a bone tunnel having a rectangular opening is formed.
Figure 17A:
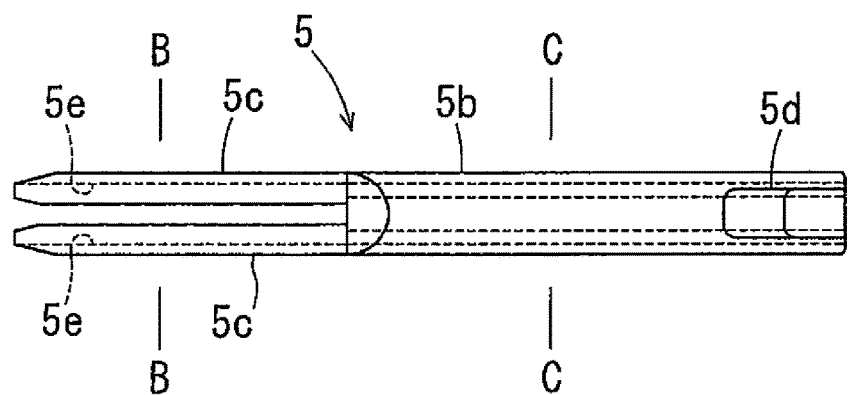
FIG. 17A is a plan view of the center drill guide.
Figure 17B:
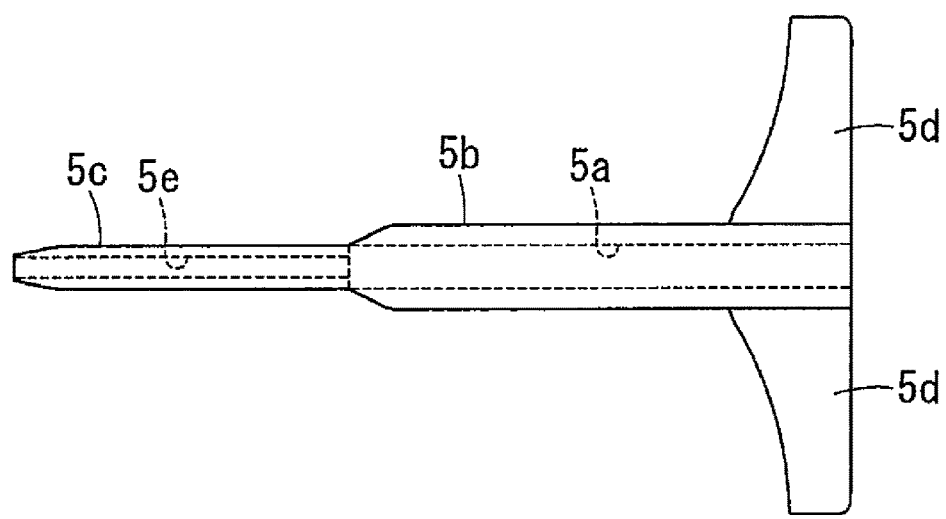
FIG. 17B is a side view of the center drill guide.
Figure 17C:
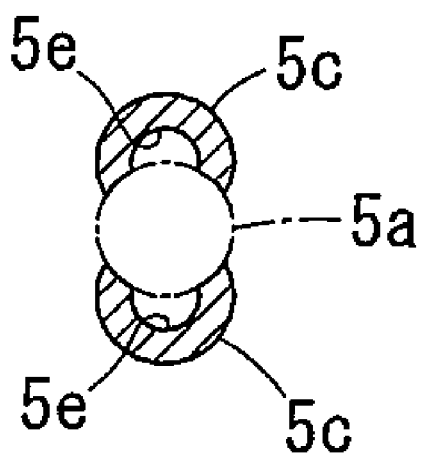
FIG. 17C is an enlarged end view of cutting FIG. 17A along the line B-B.
Figure 17D:
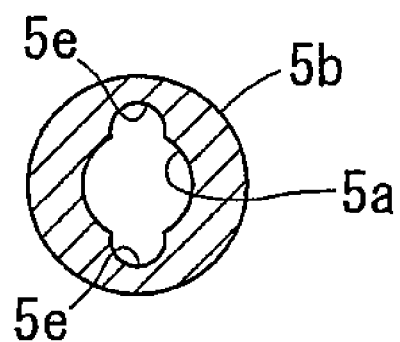
FIG. 17D is an enlarged end view of cutting FIG. 17A along the line C-C.

After the bone tunnels 4, 4 have been connected to each other by the link bone tunnel 4*a* in the above-described manner, as shown in FIG. 15 the connected bone tunnel is subjected to cutting with a chisel 7 into a rectangular or elliptical shape or expansion with a dilator (not shown), whereby a rectangular or elliptical bone tunnel 40 as shown in FIG. 16 is formed which is different from an existing circular bone tunnel and suitable for tendon transplantation. Since such a rectangular or elliptical bone tunnel 40 is formed, in the next step an approximately rectangular-parallelepiped-shaped bone piece, located at one end, of an transplantation tendon acquired from another part can be inserted into the bone tunnel 40 stably. And the bone piece, at the one end, of the transplantation tendon can be fixed to the bone strongly by screwing fixing screws (e.g., made of a polymer that is dissolved in and absorbed by a living body and having no screw head) through the bone piece and the inner surface of the bone tunnel 40.

A bone piece, at the other end, of the transplantation tendon is inserted into a bone tunnel that is bored through a thighbone top portion of the knee joint and fixed by screwing fixing screws through the bone piece and the inner surface of the bone tunnel.

Next, a guide pin piercing jig according to another embodiment of the invention will be described with reference to FIGS. 18-21.

Figure 18:
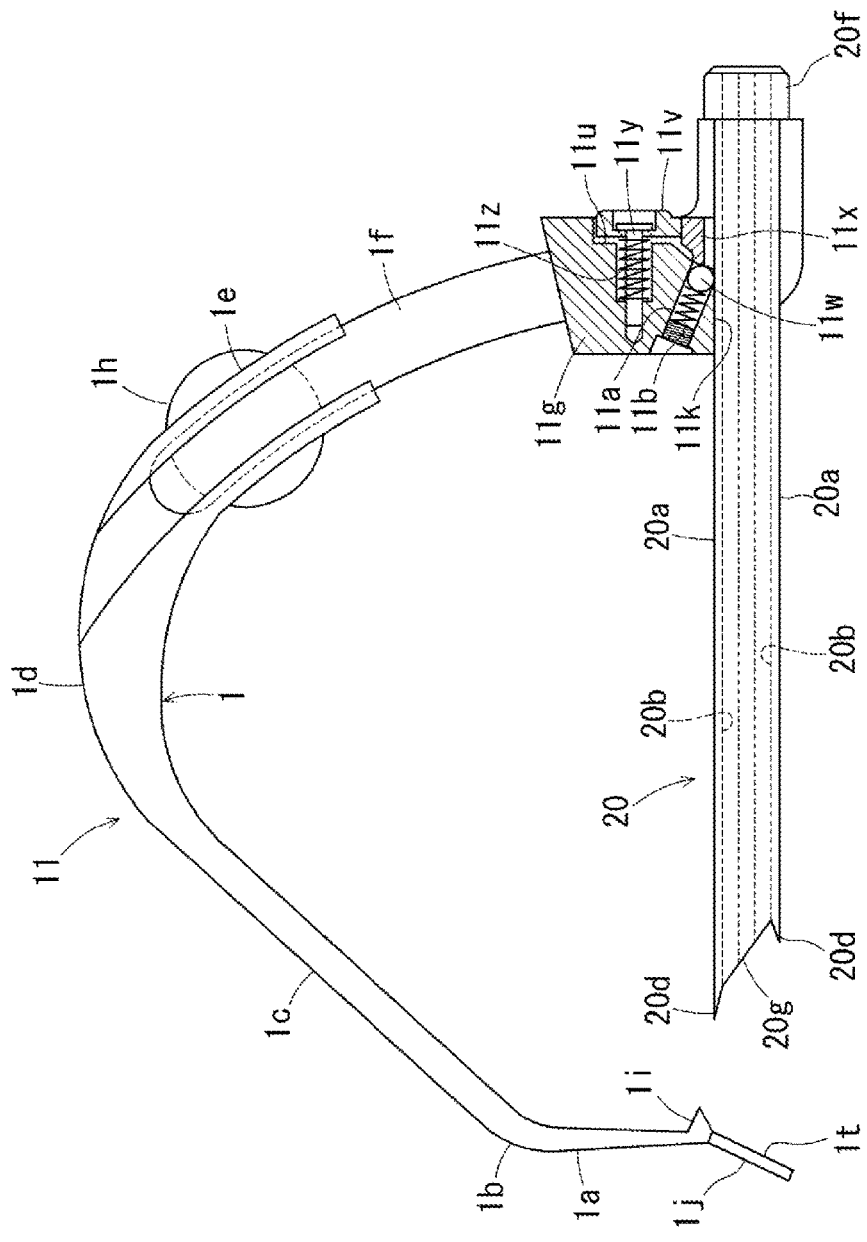
FIG. 18 is a partially sectional side view of a guide pin piercing jig according to another embodiment of the invention.
Figure 19:
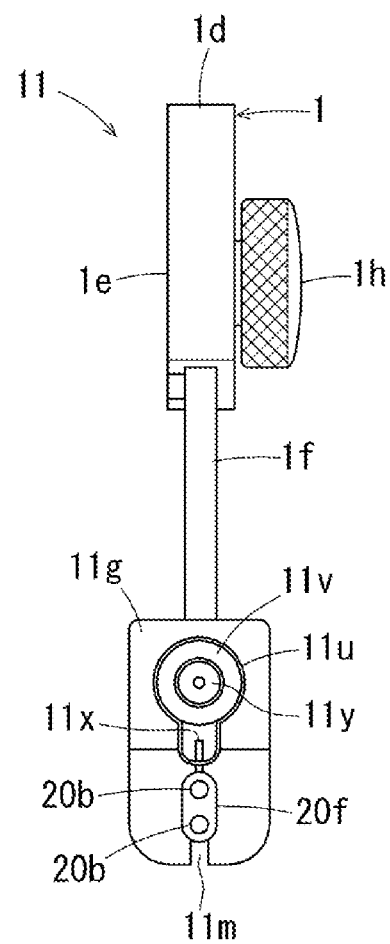
FIG. 19 is a rear view of the guide pin piercing jig.
Figure 20A:
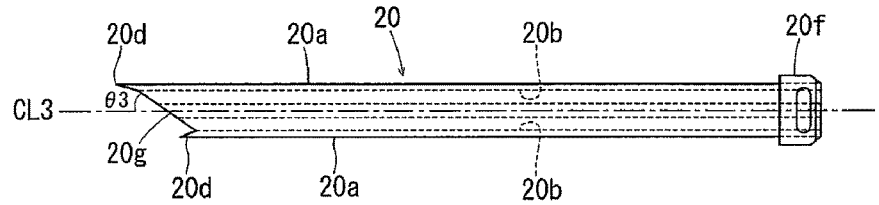
FIGS. 20A-20E are a side view, a plan view, a bottom view, a front view, and a rear view, respectively, of another example cylinder unit.
Figure 20B:
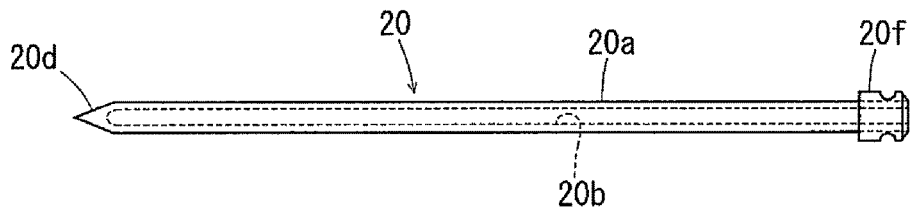
Figure 20C:
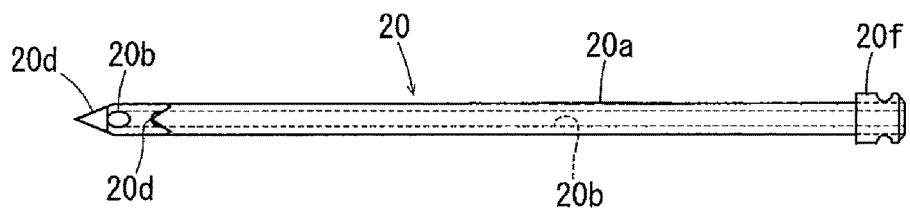
Figure 20D:
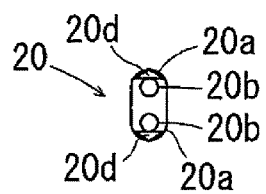
Figure 20E:
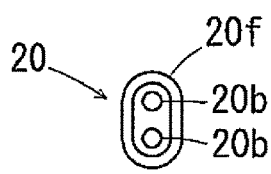
Figure 21:
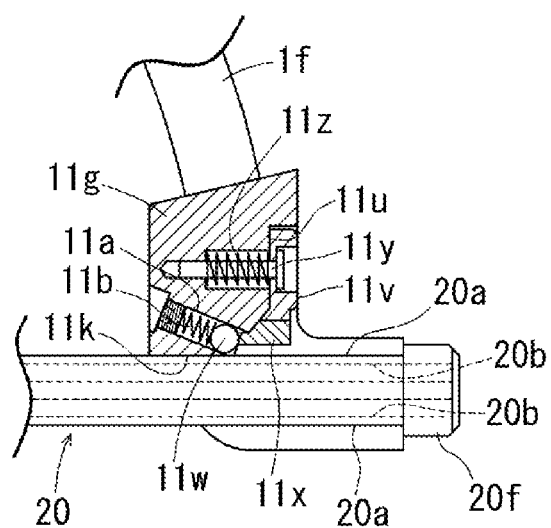
FIG. 21 is a sectional view of part of the guide pin piercing jig and shows a state that the cylinder unit is unlocked so as to be slidable rearward.

FIG. 18 is a partially sectional side view of a guide pin piercing jig according to the other embodiment of the invention, FIG. 19 is a rear view of the guide pin piercing jig, FIGS. 20A-20E are a side view, a plan view, a bottom view, a front view, and a rear view, respectively, of another example cylinder unit, and FIG. 21 is a sectional view of part of the guide pin piercing jig and shows a state that the cylinder unit is unlocked so as to be slidable rearward.

The guide pin piercing jig 11 according to this embodiment is different from the guide pin piercing jig 10 according to the above embodiment in the configurations of a rear-end attachment portion 11*g* of a frame 1 and a cylinder unit 20.

More specifically, as shown in FIGS. 18 and 20A-20E, in the rear cylinder unit 20 of this embodiment, plural (two) guide pin insertion cylinders 20*a*, 20*a* having straight cylinder holes 20*b*, 20*b* through which to insert guide pins, respectively, are provided integrally with each other and so as to extend parallel with each other and to be arranged vertically. The cylinder unit 20 is a flat cylinder unit which has an elliptical sectional shape longer in the vertical direction and contains the two parallel cylinder holes 20*b*, 20*b* through which to insert guide pins. As shown in FIG. 20A, a tip surface 20*g* of the cylinder unit 20 is inclined from the center line CL3 of the cylinder unit 20 by an angle θ3, specifically 30° to 80°. Sharp triangular projection pieces 20*d*, 20*d* as tentative fixing units project from the top end and bottom end of the tip surface 20*g*. A rear end portion of the cylinder unit 20 is a stopper portion 20*f* which is one-size thicker.

The position of the projection piece 20*d* as a tentative fixing unit is not limited to the top end and bottom end of the tip surface 20*g* of the cylinder unit 20 and may be around middle positions between the top end and bottom end of the tip portion 20*g* in the vertical direction (around middle positions between the tip opening of the top cylinder hole 20*b* and the tip opening of the bottom cylinder hole 20*b*) on the tip surface 20*g* of the cylinder unit 20.

As shown in FIGS. 20A-20E, the cylinder unit 20 is a flat cylinder unit which has an elliptical sectional shape longer in the vertical direction and contains the two parallel cylinder holes 20*b*, 20*b* through which to insert guide pins, and has the guide pin insertion cylinders 20*a*, 20*a* which are integral with each other, extend parallel with each other, and are arranged vertically (in the top-bottom direction). The cylinder unit 20 is preferable to the above-described cylinder unit 2 which has the two separate guide pin insertion cylinders 2*a*, 2*a* because the cylinder unit 20 has a larger cross section and is less prone to be deformed by stress and its center line (axis) CL3 is less prone to deviate from the boring aiming portion 1*j*.

In the case of the guide pin insertion cylinders 2*a*, 2*a* which are separate members, a slight deviation may occur between their center lines (axes) CL2 and affect guide pins 3, 3 inserted therein to cause deviations from the boring aiming portion 1*j*. In contrast, a cylinder unit like the cylinder unit 20 shown in FIGS. 20A-20E in which the two guide pin insertion cylinders 20*a*, 20*a* are integral and parallel with each other is preferable because guide pins 3, 3 inserted therein are also kept parallel with each other and hence can reach the boring aiming portion 1*j* accurately. Furthermore, in a cylinder unit like the cylinder unit 20 shown in FIGS. 20A-20E in which the two guide pin insertion cylinders 20*a*, 20*a* are integral each other, the guide pin piercing jig 11 can be fixed to a shinbone top portion 30 by sliding the only one cylinder unit 20, that is, unlike in the above-described case it is not necessary to slide the two guide pin insertion cylinders 2*a*, 2*a* individually. Therefore, the fixing work can be carried out in a short time and the number of components is reduced. As a result, work of attaching the cylinder unit 20 to the attachment portion 11*g* and detaching the former from the latter can be carried out simply in a short time.

If a flat cylinder unit which has an elliptical sectional shape longer in the vertical direction and contains only one guide pin insertion cylinder extending along the center line is manufactured separately in advance, the jig 11 can also be used in the case of forming an existing, single circular bone tunnel rather than an elliptical one.

The reason why as described above the tip surface 20*g* of the cylinder unit 20 is inclined by the angle 30° to 80° is to allow the cylinder unit 20 to be fixed to the front surface of a shinbone top portion 30 tentatively by means of the tentative fixing unit 20*d* with its tip surface 20*g* conforming to the front surface of the shinbone top portion 30 stably in ACL reconstruction. In the cylinder unit 20 of the embodiment, the inclination angle θ3 is set at 35°. The cylinder unit 20 in which the tip surface 20*g* is inclined by 35° is a typical cylinder unit that is suitable for a shinbone, and a preferable range is 30° to 50°. A cylinder unit 20 in which the tip surface 20*g* is inclined by 65° is also used for living bodies of a certain type. Cylinder units 20 in which the tip surface 20*g* is inclined in a range of 50° to 80° can also be used in the case of boring a bone tunnel through a thighbone. That is, where the inclination angle of the tip surface 20*g* of the cylinder unit 20 is in the range of 50° to 80°, when the boring aiming portion 1*j* is applied to a portion, to which to bore a tunnel, of the inside of the joint (at a far end of the thighbone) and the tip surface 20g of the cylinder unit 20 is brought into contact with the front surface of an outside top bulge of the thighbone, the cylinder unit 20 can be fixed to the outside top bulge of the thighbone tentatively by the tentative fixing units 20d, 20d with the tip surface 20g conforming to the front surface of the outside top bulge of the thighbone stably.

On the other hand, as shown in FIGS. 18, 19, and 21, the rear-end attachment portion 11g of the frame 1 is formed with a button housing recess 11u which houses a push button 11v. The push button 11v is provided with a pusher 11x for pushing a sphere 11w as described later at the bottom. A screw 11y is screwed into a screw hole through a center hole of the push button 11v and the inside space of a compression coil spring 11z disposed behind the push button 11v. The push button 11v is urged by the compression coil spring 11z in such a direction as to be pushed out. Therefore, a certain gap is secured between the push button 11v and the bottom face of the button housing recess 11u and the push button 11v can be pushed in against the resilient force of the compression coil spring 11z until hitting the bottom face of the button housing recess 11u.

An insertion hole 11k having a vertically long, elliptical sectional shape (and being continuous with a slit 11m at the bottom as shown in FIG. 19) into which to insert the cylinder unit 20 is formed through a bottom portion of the attachment portion 11g so as to extend toward the tip boring aiming portion 1j of the frame 1. A communication hole 11a which communicates with the insertion hole 11k from obliquely above houses the sphere 11w and a compression coil spring 11b. Because of the resilient force of the compression coil spring 11b, the sphere 11w is in contact with the tip of the pusher 11x and projects slightly into the insertion hole 11k. When the push button 11v is pushed by a fingertip, the pusher 11x is moved together with the push button 11v and pushes the sphere 11w to the deep side in the communication hole 11a.

Therefore, when the cylinder unit 20 is inserted into the insertion hole 11k of the attachment portion 11g from behind, the sphere 11w is pushed up by the cylinder unit 20 and goes inward in the communication hole 11a. As a result, as shown in FIG. 18, the cylinder unit 20 can be inserted into the attachment portion 11g until the stopper portion 20f of the cylinder unit 20 hits the wall surface of the attachment portion 11g. On the other hand, an attempt to pull out the cylinder unit 20 fails because the sphere 11w bites into the tip of the pusher 11x and the top surface of the cylinder unit 20 as if to go into a gap formed between them.

In contrast, as shown in FIG. 21, when the push button 11v is pushed with a fingertip, the pusher 11x is moved together with the push button 11v and the tip of the pusher 11x pushes the sphere 11w to the deep side in the communication hole 11a against the resilient force of the compression coil spring 11b and hence the cylinder unit 20 can be pulled out easily. A button-cancellation ball-type stopper is thus formed.

The above-described stopper in which the push button 11v is provided in the button housing recess 11u which is formed in the rear end surface of the attachment portion 11g is preferable because it is free of a probability that the push button 11v is touched inadvertently during an operation and the fixing of the cylinder unit 20 is thereby canceled.

In the type of stopper shown in FIG. 1 in which the ratchets 2e, 2e of the guide pin insertion cylinders 2a, 2a are engaged with the respective engagement projections 1n, 1n and the engagement is canceled by rotating the guide pin insertion cylinders 2a, 2a by 180°, the guide pin insertion cylinders 2a, 2a need to have a circular sectional shape. The above-described button-cancellation ball-type stopper is preferable because it also enables use of cylinder units 20 having sectional shapes other than a circle.

The slit 11m which is formed under the insertion hole 11k serves, in ACL reconstruction, to take out guide pins 3, 3 downward in removing the frame 1 from a shinbone top portion 30 that is pierced with the guide pins 3, 3 after pulling the cylinder unit 20 out of the insertion hole 11k.

The other part of the configuration of the guide pin piercing jig 11 according to this embodiment is the same as the corresponding part of the guide pin piercing jig 10 according to the above embodiment, and hence will not be described redundantly by assigning the same symbols to the same members shown in FIGS. 18 to 21.

In ACL reconstruction, like the guide pin piercing jig 10 according to the above embodiment, the guide pin piercing jig 11 according to this embodiment enables the following work. The tip portions of the frame 1, that is, the boring aiming portion 1j and the tip arm 1a, are inserted into the knee joint from the front side. The contact surface 1t of the boring aiming portion 1j is positioned by applying it to a proper portion, to which to bore a bone tunnel, of a recessed top surface 30a of a shinbone top portion 30 and sticking the positioning projection 1i into the top surface 30a. The cylinder unit 20 is fixed tentatively so as to be oriented in a proper direction intended by a doctor by sticking, into the front surface of the shinbone top portion 30, the sharp tip projection pieces 20d, 20d of the cylinder unit 20 that is inserted in the insertion hole 11k of the attachment portion 11g of the frame 1. The shinbone top portion 30 is pierced with two guide pins 3, 3 inserted through the two respective guide pin insertion holes 20b, 20b until they reach the boring aiming portion 1j. In this manner, the two guide pins 3 for hollow drills can pierce the shinbone top portion 30 in a proper direction to a proper portion to which to bore a bone tunnel according to the intention of the doctor, so as to extend parallel with each other and to be arranged vertically. Subsequently, two bone tunnels 4, 4 are bored through the shinbone top portion 30 by the hollow drills along the respective guide pins 3, 3. The two bone tunnels 4, 4 are connected to each other by boring a tunnel 4a between them, and a connected bone tunnel is subjected to cutting into a rectangular or elliptical shape. As a result, a rectangular or elliptical bone tunnel that is suitable for tendon transplantation can be formed through the shinbone top portion 30.

Although the invention has been described in detail by referring to the particular embodiments, it is apparent to those skilled in the art that various changes and modifications are possible without departing from the spirit and scope of the invention.

The present application is based on Japanese Patent Application No. 2013-241762 filed on Nov. 22, 2013, the disclosure of which is incorporated herein by reference.

The invention claimed is:

1. A guide pin piercing jig for piercing a living body bone with guide pins for boring hollow drills in such a manner as to determine positions and a direction of the guide pins, the guide pin piercing jig comprising:
 a frame having a positioning projection at a tip thereof;
 a bore aiming portion at a vicinity of the positioning projection; and
 a cylinder unit,
 wherein the cylinder unit is configured to integrate a plurality of parallel guide pin insertion cylinders with each other and has a tentative fixing unit at a tip of the cylinder unit and is attached to the frame slidably so as to be directed to the tip of the frame, wherein the tip of the cylinder unit is inclined from a center line thereof by 30° to 80° so that one of the guide pin insertion cylinders that is located closer to the frame is longer than another of the guide pin insertion cylinders that is located farther away from the frame, and wherein the bore aiming portion has a through hole through which axial center lines of the plurality of parallel guide pin insertion cylinders pass.

2. The guide pin piercing jig according to claim 1, wherein an angle at which a center line of an inside surface of a tip arm of the frame and center lines of the guide pin insertion cylinders cross each other is in a range of 60° to 90°.

3. The guide pin piercing jig according to claim 1, wherein a surface, to be brought into contact with a living body bone, of the boring aiming portion is inclined from a center line of an inside surface of a tip arm of the frame by 5° to 30°.

4. The guide pin piercing jig according to claim 1, wherein the cylinder unit is detachable from the frame.

5. The guide pin piercing jig according to claim 1, wherein a length of a tip arm of the frame is in a range of 10 to 50 mm.

6. The guide pin piercing jig according to claim 1, wherein the frame has a bent portion, which is located at a position that is distant from the tip of the frame by 10 to 50 mm and bent at 30° to 80°, and a tip arm, which extends straightly from the bent portion to the tip of the frame.

\* \* \* \* \*